United States Patent [19]

Hosch et al.

[11] 4,381,136

[45] Apr. 26, 1983

[54] METHOD FOR COVERING ULTRAVIOLET SOURCES

[75] Inventors: Ludwig Hosch, Darmstadt; Guenther Ittmann, Gross-Umstadt, both of Fed. Rep. of Germany

[73] Assignee: Röhm GmbH, Darmstadt, Fed. Rep. of Germany

[21] Appl. No.: 239,910

[22] Filed: Mar. 3, 1981

[30] Foreign Application Priority Data

Mar. 5, 1980 [DE] Fed. Rep. of Germany ....... 3008364

[51] Int. Cl.³ .............................................. G02B 5/22
[52] U.S. Cl. ..................................... 350/1.1; 350/311; 350/320
[58] Field of Search .................. 250/504, 505.1; 350/311, 1.1, 320

[56] References Cited

U.S. PATENT DOCUMENTS

1,945,567  2/1934  Rolph ................................ 250/504
4,167,490  9/1979  Looney .............................. 252/300

FOREIGN PATENT DOCUMENTS

2609194  9/1977  Fed. Rep. of Germany .
2714696  10/1978  Fed. Rep. of Germany .
2911758  10/1980  Fed. Rep. of Germany .

OTHER PUBLICATIONS

Pasco et al., Optics and Laser Technology 10, 71-76 (1978).

*Primary Examiner*—Bruce Y. Arnold
*Attorney, Agent, or Firm*—Curtis, Morris & Safford

[57] ABSTRACT

Disclosed is a method for covering a source emitting ultraviolet radiation which method comprises covering said source with an acrylic glass colored with a coloring agent which absorbs in the visible region of the spectrum between 400 nanometers and 550 nanometers and exhibits an absorption of at least 2 percent for any wavelength within this region, and which agent concurrently has an average degree of transmission in the A- and B-region of the ultraviolet spectrum which is not below 55 percent and is not less than 10 percent at any wavelength in this region, said agent being present at a concentration equivalent to 0.0005 to 0.3 percent by weight in a layer, one millimeter thick, of a radiation absorbing matrix. Also disclosed are colored acrylic glass covers for use in such a method.

15 Claims, 1 Drawing Figure

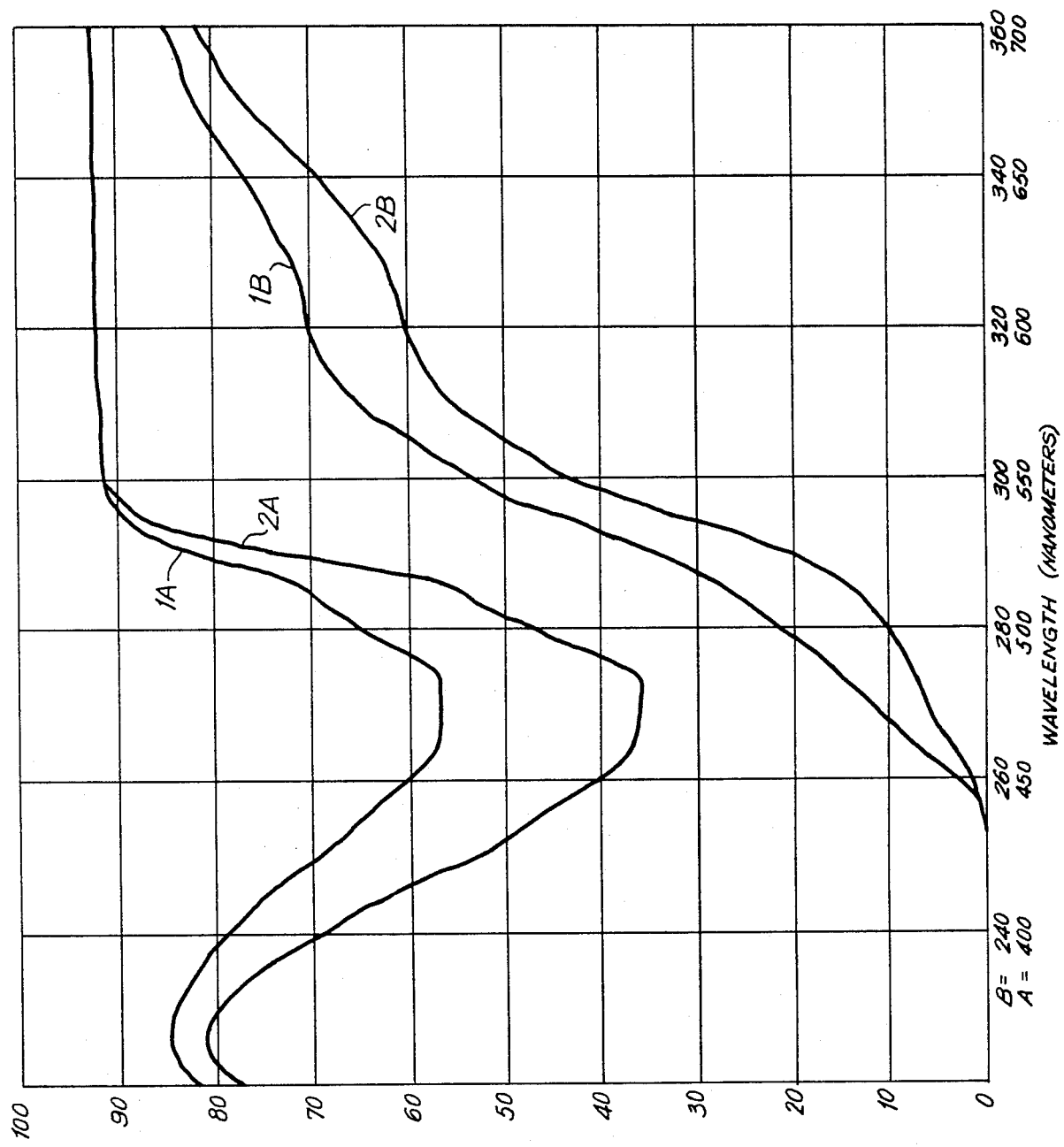

METHOD FOR COVERING ULTRAVIOLET SOURCES

The present invention relates to methods for covering a source emitting ultraviolet radiation with a colored acrylic glass and to such a colored acrylic glass cover.

Acrylic glasses are suitable as covers for light sources which emit ultraviolet light (ultraviolet radiators). Prerequisites for suitability as a cover material for ultraviolet sources are, on the one hand, the greatest possible transparency for ultraviolet light of the desired wave length region and, on the other hand, a sufficient insensitivity of the cover material to ultraviolet radiation.

Ultraviolet radiators have acquired a particular significance in the field of health care where they have found wide dissemination as "artificial suns", "sun lamps" and, earlier, as solaria.

As ultraviolet radiators, high pressure mercury lamps, for example, and—to an increasing degree—low pressure mercury vapor lamps are being used. By the use of suitable filters, regions of the ultraviolet spectrum which are questionable from the health standpoint can be eliminated from the ultraviolet light which is permitted to act. In the use of ultraviolet irradiation in the field of health care or for cosmetic uses, there is a tendency to limit the ultraviolet radiation to the spectral region, unobjectionable from a health viewpoint, between 400 and 315 nanometers (nm) (ultraviolet A-region) and to certain portions of the region between 315 and 280 nm (ultraviolet B-region). The "hard" ultraviolet C-region between 280 and 200 nm should be excluded as completely as possible. Efforts are directed to maintaining the ultraviolet B-portion of the ultraviolet light which is effectively applied to an order of magnitude of 0.04 percent, as in sunlight.

In addition to the ordinary ultraviolet sources comprising movable ultraviolet radiators, which are intended more for a partial irradiation of the body, so-called "solarium benches" have been developed in which the human body lies above the radiation source during irradiation, using a cover on the source as a surface on which to lie. According to information provided by the manufacturer of such devices, great attention has been paid to the choice of the advantageous ultraviolet region in an effort to achieve the advantageous effects of exposure to the sun (anti-rachitic effect, tanning, etc.) without having at the same time to suffer any disadvantages from a health viewpoint. A particular advantage in the use of acrylic glass as a covering for such "solarium benches", for example, apart from its transparency to electromagnetic radiation down to about 260 nm, is that this material is pleasant to the touch because of its low thermal conductivity. In addition there is the lack of sensitivity to breakage and the easy workability of acrylic glasses, which glasses, in case of need, can also be crosslinked.

In any event, the ultraviolet irradiation arrangements of the state of the art in general leave something to be desired in one particular effect. That is, the visible light emitted by ultraviolet radiators is, because of its spectral composition, experienced by the human eye as "unnaturally blue" and as "unpleasantly cold". From this impression, an explicit or implicit prejudice against the use of ultraviolet light for health care or cosmetic purposes can result.

It has now been found that materials comprising acrylic glass for coating ultraviolet-emitting radiation sources, which materials avoid the aforementioned difficulty, are obtained if the acrylic glass contains a coloring agent, either in homogeneous distribution therein or in the form of a surface coloration subsequently applied from an immersion bath, as a lacquer coating, or as a component of a colored film. The coloring agent absorbs in the visible spectrum between 400 and 550 nm of the electromagnetic spectrum and has an absorption of at least 2 percent for a wave length within this region. Concurrently, it has an average spectral degree of transmission, $T\lambda$, in the ultraviolet A-region and in the ultraviolet B-region, of not less than 55 percent, at a concentration equivalent to 0.0005 to 0.3 percent by weight in a layer, one millimeter thick, of a radiation-absorbing matrix, assuming constant transmission as a function of thickness (adherence to the Lambert-Beer law). At no wavelength within this region does the coloring agent have a degree of transmission of less than 10 percent at a concentration as specified.

A coloring agent content equivalent to 0.003 to 0.1 percent by weight of the specified matrix is particularly preferred.

Preferably, a coloring agent is used which has a degree of transmission at 300 nm of at least 20 percent and a degree of transmission at 320 nm of at least 50 percent.

BRIEF DESCRIPTION OF THE DRAWING

The drawing shows the transmission (in percent) of the acrylic glass materials of Examples 3 and 4, each containing "Makrolexorange GG" dyestuff, in the ultraviolet A- and B-region as a function of wavelength (in nanometers). (This dye is also known as "Solvent Orange 54".) The "1A" and "1B" curves are for a dye concentration of 0.00083 percent by weight and the "2A" and "2B" curves are for a dye concentration of 0.00166 percent by weight; in both cases the dye is present in a 6 mm thick layer of acrylic glass.

DETAILED DESCRIPTION OF THE INVENTION

The term "coloring agents", as employed above and hereinafter, should be understood according to the invention as referring to substances which are compatible with and homogeneously distributable in an acrylic glass and which have the desired selective spectral absorption, and includes not only soluble dyes but also pigments. In addition, the term includes dyes and pigments which are suitable as components of lacquers or films which can be applied to an acrylic glass surface and to dyes and pigments which can be taken up into the surface of the acrylic glass by an immersion process.

The coloring agents which contribute the desired properties are known per se. For a transparent coloration of acrylic glasses, in general, organic dyes which are truly soluble in the polymer or which are colloidally soluble are used. These dyes are limited to a very small selection, for example azo dyes and anthraquinone dyes, as well as certain metal complex dyes. Specifically, the following are particularly suitable as soluble dyestuffs for the coloration of acrylates: "Thermoplast", "Neozapon", and fat-soluble dyes such as the "Sudan" dyes (prepared by BASF); "Macrolex" and "Ceres" dyes (manufactured by Bayer); "Waxoline" dyes (prepared by ICI); "Solvaperm" dyes and fatty dyes (prepared by Hoechst); and the "Orasol" or "Oracet" and "Mikrolith" dyes (prepared by Ciba-Geigy).

Those coloring agents are preferred which have an absorption, depending on wavelength, which is such that the light penetrating the acrylic glass cover is experienced by the human eye as being in the range from yellow to orange or red. Preferred for this purpose are coloring agents selected from the group of anthraquinone dyestuffs, monoazo dyestuffs, and chromium-complex dyestuffs. The coloring agents "Makrolexorange GG" (Bayer) comprising an anthraquinone dye 1,4-dihydroxy-anthraquinone ("Chinizarin") (Color Index No. 58 050); "Neozaponorange RE" a chromium-complex dye manufactured by BASF (Color Index="Solvent Orange 54"); and "Solvapermorange 54", manufactured by Hoechst, are preferably added.

Preferably, stabilizers, including light-protective agents and thermal stabilizers, are added according to the invention to the acrylic glass to be used. The amount of these agents is, as a rule, from 0.01 to 1 percent by weight of the polymer into which they are incorporated. Sterically hindered amines, particularly piperidine compounds such as bis-(2,2,6,6-tetramethyl-4-piperidyl)sebacate, are preferred. The stabilizers, inclusive of light-protective agents and thermal stabilizers, particularly protect acrylic glass polymers against the effects of electromagnetic radiation in the region from 300 to 800 nm. They are intended to protect the polymers against the destructive effects of the radiation, namely a degradation of the polymers into monomeric or oligomeric fragments containing double bonds, which degradation brings about a yellowing of the polymers and the formation of material inhomogeneities and tension cracks therein. Under the influence of deposits of perspiration, sun tan oils, perfume, alcohol, and the like, such tension cracks can lead to corrosion of the acrylic glass cover of a solarium bench.

Acrylic glasses of the kind which are claimed herein as covers are known per se, as are methods suitable for shaping the materials [cf. R. Vieweg et al., Kunststoff-Handbuch ("Plastics Handbook"), Vol. IX, "Polymethacrylate" ("Polymethacrylates"), Carl Hanser Verlag 1975]. Acrylic glasses which are homopolymers or copolymers of methyl methacrylate are particularly mentioned. As comonomers, for example, further esters of methacrylic acid or esters of acrylic acid, particularly those of $C_1$-$C_3$ alcohols, are considered. Similarly suitable are vinyl esters of alkanoic acids, e.g. vinyl acetate. The use of these materials is limited in each case by their transparency in the ultraviolet region.

Polymerization can suitably be carried out according to a flat chamber process [Kunststoff-Handbuch, (Plastics Handbook), Vol. IX, loc. cit.]. When the matrix is homogeneously colored, the coloring agent and the light protective agent or stabilizer are stirred in, optionally with a crosslinking agent, with the necessary polymerization initiators, such as azo-accelerators and/or per-esters, which themselves should not absorb in the ultraviolet.

The content of initiator is related, within certain limits, to the thickness of the acrylic glass sheet prepared. In general, it is between 0.01 and 0.2 percent by weight of the monomers employed.

In general, the polymerization is carried out in a water bath at a temperature between 30° C.–60° C. and is concluded in a warming oven at a temperature between 90° C. and 120° C.

As crosslinking agents, monomers known in the art having at least two double bonds capable of polymerization reactions are to be considered. Glycol dimethacrylate, or allyl compounds such as triallyl cyanurate or allyl methacrylate, should be mentioned. The amount of the crosslinking agents can be between 0.01 and 10 percent, by weight of all the monomers. Although crosslinking agents influence the mechanical properties of the polymer, they are used principally to improve the resistance of the polymer to corrosion under the influence of perspiration, sun tan lotions, etc. They also improve the resistance of the polymer to thermal distortion.

Methods for the coloring of acrylic glasses are known in the prior art [cf. "Kunststoff-Handbuch," Vol. IX, loc cit.]. The application of a coloring agent to polymer surface can also be carried out by methods known in the art. Lacquering can be performed by means known in the art, for example by painting, screen printing, or immersion into a lacquer composition.

A better understanding of the present invention and of its many advantages will be had by referring to the following specific Examples, given by way of illustration.

The drawing shows the transmission (in percent) of the acrylic glass materials of following Examples 3 and 4, each containing "Makrolexorange GG" dyestuff, in the ultraviolet A- and B-region as a function of wavelength (in nanometers). (This dye is also known as "Solvent Orange 54".) The "1A" and "1B" curves are for a dye concentration of 0.00083 percent by weight and the "2A" and "2B" curves are for a dye concentration of 0.00166 percent by weight; in both cases the dye is present in a 6 mm thick layer of acrylic glass.

EXAMPLES 1–7: COLORATION OF THE MATRIX

Basic batch formula:

| | |
|---|---|
| 120 g | of methyl acrylate, |
| 4 g | of bis-(2,2,6,6-tetramethyl-4-piperidyl)-sebacate, |
| 1 g | of azoisobutyric acid dinitrile, and |
| 875 g | of methyl methacrylate. |
| 1000 g | |

For each Example, polymerization of the 1000 g basic batch is carried out, after the addition of the coloring agents and auxiliaries mentioned, in a flat chamber between silicate glass plates spaced 6 mm apart at a temperature between 40° C. and 60° C. within about 20 hours in a bath. The material is then finally polymerized over a period of 6 to 10 hours at a temperature between 90° C. and 120° C.

Yellow- to orange-colored, clear, transparent sheets are obtained which, optionally after cutting to the required dimensions, can be used, for example, as covers for solarium benches or lamps, or can be used in the construction industry, for example as roofing for sun porches.

EXAMPLE 1

0.0083 g of "Neozaponorange RE" are dissolved in the aforementioned basic batch and the batch is polymerized in a layer thickness of 6 mm. [The actual concentration of the dye in the 1000 g batch is 0.00083 percent by weight present in a layer thickness of 6 mm. The equivalent concentration in a layer one millimeter thick would be 6×0.00083, or 0.00498 percent by weight.]

EXAMPLE 2

0.0166 g of "Neozaponorange RE" are dissolved in the basic batch and are polymerized in a layer thickness of 6 mm.

EXAMPLE 3

0.0083 g of "Macrolexorange GG" are dissolved in the basic batch are polymerized in a layer thickness of 6 mm.

EXAMPLE 4

0.0166 g of "Macrolexorange GG" are dissolved in the basic batch and are dissolved in a layer thickness of 6 mm.

EXAMPLE 5

2 g of triallyl cyanurate are added as a crosslinking agent to the basic batch, 0.0083 g of "Neozaponorange RE" are dissolved therein, and the batch is polymerized in a layer thickness of 6 mm.

EXAMPLE 6

2 g of triallyl cyanurate are added as a crosslinking agent to the basic batch, 0.0083 g of "Macrolexorange GG" are also added, and the batch is polymerized in a layer thickness of 6 mm.

EXAMPLE 7

1 g of glycol dimethacrylate as a crosslinking agent and 0.0083 g of "Macrolexorange GG" are added and dissolved, respectively, in the basic batch and the batch is polymerized in a layer thickness of 6 mm.

The results of measurements on the samples for resistance to deformation by heat according to the Vicat softening temperature (VST) are reported below, as are values for their transmission (in percent) at 300 nm before irradiation and after irradiation for different periods of time (72, 250, and 1000 hours) with solarium light sources [lamp type UVA=Solarium A 1.00, 80 w, 8Z (Wolf-system) and UVB=Helarium B 1.01, 80 w, 8U (Wolf-system)].

TABLE

| Example | VST (°C.) | Ultraviolet Lamp Type A | Ultraviolet Lamp Type B | Light Transmission (in percent at 300 nm) Before irradiation | After irradiation 72 h. | After irradiation 250 h | After irradiation 1000 h |
|---|---|---|---|---|---|---|---|
| (1) | 103 | A | | 59 | 57 | 59 | 62 |
|     |     |   | B | 60 | 58 | 59 | 62 |
| (2) | 103 | A | | 50 | 48 | 50 | 53 |
|     |     |   | B | 50 | 47 | 49 | 52 |
| (3) | 101 | A | | 62 | 57 | 60 | 63 |
|     |     |   | B | 62 | 60 | 63 | 64 |
| (4) | 103 | A | | 58 | 52 | 54 | 55 |
|     |     |   | B | 58 | 54 | 55 | 55 |
| (5) | 103 | A | | 58 | 54 | 57 | 58 |
|     |     |   | B | 58 | 54 | 54 | 55 |
| (6) | 102 | A | | 63 | 57 | 59 | 60 |
|     |     |   | B | 62 | 58 | 59 | 59 |
| (7) | 102 | A | | 65 | 58 | 61 | 64 |
|     |     |   | B | 65 | 59 | 62 | 64 |

EXAMPLE 8: (A) SURFACE COLORATION

The material to be colored, which is a colorless acrylic glass prepared from a basic batch as in the previous Examples, is immersed in the corresponding dye solutions according to the desired strength of color.

Solution I—0.5 g of "Oracetgelb 5GN" Color Index=Solvent Yellow 35S, previously dissolved in 300.0 g of acetone, is combined with 200.0 g of distilled $H_2O$.

Solution II—0.25 g of "Oracetorange 2R" Color Index=Solvent Red 9=$CI_{II}11005$, previously dissolved in 300.0 g of acetone, is combined with 200.0 g of distilled water.

| Solution | Immersion Time (seconds) | Temperature of the solution | Appearance of the resulting acrylic glass |
|---|---|---|---|
| I  | 5  | 40° C. | Very bright glowing yellow |
| I  | 20 | 40° C. | Bright yellow, clear |
| II | 5  | 40° C. | Very bright orange |
| II | 10 | 40° C. | Orange, clear |

(B) LACQUERING

Lacquer: 0.1 g of "Makrolexorange GG" is dissolved in 100 g of an acrylic resin lacquer which is transparent to ultraviolet, or in a nitro lacquer.

A suitable amount of the lacquer, depending on the degree of the desired color nuance, is applied to a colorless acrylic glass sheet made from the material of the basic batch described above. Application can be by painting. Alternatively, the material may also be immersed, sprayed, or screen printed.

"Zaponechtorange RE" (="Solvent Orange 54") can be used as a coloring agent in any of Examples 1-8 with comparable results.

The optically detectible results obtained using a stabilized acrylic glass copolymer, as in the Examples, are obtained also with stabilized homopolymeric methyl methacrylate or with unstabilized homopolymers and copolymers of methyl methacrylate. The stabilized materials are preferred, however, since they show a substantially constant transmission in the ultraviolet A- and B-region throughout long periods of use.

What is claimed is:

1. A method for covering a source emitting ultraviolet radiation which comprises covering said source with an acrylic glass colored with a coloring agent which absorbs in the visible region of the spectrum between 400 nanometers and 550 nanometers and exhibits an absorption of at least 2 percent for a wavelength within this region, and which agent concurrently has an average degree of transmission in the A- and B-region of the ultraviolet spectrum which is not below 55 percent and is not less than 10 percent at any wavelength in this region, said agent being present at a concentration equivalent to 0.0005 to 0.3 percent by weight in a layer, one millimeter thick, of a radiation absorbing matrix.

2. A method as in claim 1 wherein said agent has a degree of transmission of at least 20 percent at 300 nanometers and a degree of transmission of at least 50 percent at 320 nanometers.

3. A method as in claim 1 wherein said agent is a member selected from the group consisting of anthraquinone, azo, and chromium-complex dyestuffs.

4. A method as in claim 1 wherein said agent is present at a concentration equivalent to 0.003 to 0.1 percent by weight in a layer, one millimeter thick, of a radiation-absorbing matrix.

5. A method as in claim 1 wherein said agent absorbs radiation such that light from said covered source is experienced by the human eye as yellow to red in color.

6. A method as in claim 1 wherein said agent is present incorporated within said acrylic glass.

7. A method as in claim 6 wherein said acrylic glass additionally comprises at least one member selected from the group consisting of stabilizers and crosslinking agents.

8. A method as in claim 7 wherein said stabilizers are sterically-hindered amines.

9. A method as in claim 8 wherein said sterically-hindered amines are piperidine compounds.

10. A method as in claim 6 wherein said acrylic glass additionally comprises bis-(2,2,6,6-tetramethyl-4-piperidyl) sebacate as a stabilizer.

11. A method as in claim 1 wherein said acrylic glass is a polymer comprising methyl methacrylate.

12. A method as in claim 1 wherein said agent is present in a superficial layer in said acrylic glass.

13. A method as in claim 1 wherein said agent is present in a coating layer present on the surface of said acrylic glass.

14. A method as in claim 13 wherein said coating layer is a layer of lacquer present on said acrylic glass.

15. A cover for a source emitting ultraviolet radiation, said cover comprising an acrylic glass colored with a coloring agent which absorbs in the visible region of the spectrum between 400 nanometers and 550 nanometers and exhibits an absorption of at least 2 percent for a wavelength within this region, and which agent concurrently has an average degree of transmission in the A- and B-region of the ultraviolet spectrum which is not below 55 percent and is not less than 10 percent at any wavelength in this region, said agent being present at a concentration equivalent to 0.0005 to 0.3 percent by weight in a layer, one millimeter thick, of a radiation absorbing matrix.

* * * * *